US006753008B2

(12) United States Patent
Cheung

(10) Patent No.: US 6,753,008 B2
(45) Date of Patent: Jun. 22, 2004

(54) DIETARY SUPPLEMENTS BENEFICIAL FOR THE LIVER

(75) Inventor: Ling Yuk Cheung, New Territories (HK)

(73) Assignee: Ultra Biotech Limited, Douglas (GB)

( * ) Notice: Subject to any disclaimer, the term of this patent is extended or adjusted under 35 U.S.C. 154(b) by 0 days.

(21) Appl. No.: 10/187,112

(22) Filed: Jun. 28, 2002

(65) Prior Publication Data

US 2004/0001858 A1 Jan. 1, 2004

(51) Int. Cl.[7] .......................... A61K 47/00; C12N 13/00; C12N 1/14; C12N 1/16; C12N 1/18

(52) U.S. Cl. .................. 424/439; 424/400; 424/464; 424/489; 424/480; 424/800; 435/173.1; 435/173.8; 435/243; 435/254.1; 435/255.1; 435/255.2; 435/255.21

(58) Field of Search ..................... 424/400, 439, 424/464, 489, 780, 800; 435/173.1, 173.8, 243, 255.1, 255.2, 255.21, FOR 100, FOR 114, 254.1

(56) References Cited

U.S. PATENT DOCUMENTS

| 4,081,367 A | 3/1978 | Hulls et al. ............... 210/610 |
| 4,183,807 A | 1/1980 | Yoshizawa et al. ......... 210/611 |
| 4,211,645 A | 7/1980 | Zajic et al. ................. 210/611 |
| 4,559,305 A | 12/1985 | Zajic et al. ................. 435/243 |
| 4,816,158 A | 3/1989 | Shimura et al. ............ 210/610 |
| 5,075,008 A | 12/1991 | Chigusa et al. ............. 210/610 |
| 5,106,594 A | 4/1992 | Held et al. .................. 422/292 |
| 5,416,010 A | 5/1995 | Langenberg et al. ........ 435/468 |
| 5,476,787 A | 12/1995 | Yokoyama et al. ....... 435/262.5 |
| 5,567,314 A | 10/1996 | Chigusa et al. ............. 210/150 |
| 5,578,486 A | 11/1996 | Zhang ........................ 435/243 |
| 5,707,524 A | 1/1998 | Potter ......................... 210/606 |
| 5,879,928 A | 3/1999 | Dale et al. .................. 435/264 |
| 6,036,854 A | 3/2000 | Potter ......................... 210/177 |
| 6,391,617 B1 | 5/2002 | Cheung ...................... 435/254 |
| 6,391,618 B1 | 5/2002 | Cheung ...................... 435/255 |
| 6,391,619 B1 | 5/2002 | Cheung ...................... 435/255 |
| 6,436,695 B1 | 8/2002 | Cheung ...................... 435/254 |
| 6,440,713 B1 | 8/2002 | Cheung ...................... 435/173 |
| 2002/0123127 A1 | 9/2002 | Cheung .................. 435/254.21 |
| 2002/0123129 A1 | 9/2002 | Cheung ................... 435/254.2 |
| 2002/0123130 A1 | 9/2002 | Cheung ................... 435/262.5 |

FOREIGN PATENT DOCUMENTS

| CN | 1110317 A | 10/1995 |
| EP | 0041373 | 12/1981 |
| FR | 2222433 | 10/1974 |
| JP | 60028893 | 2/1985 |
| RU | 415983 A | 11/1974 |
| RU | 1071637 | 2/1984 |
| WO | WO 87/02705 | 5/1987 |
| WO | WO 95/04814 | 2/1995 |
| WO | WO 99/60142 | 11/1999 |
| WO | WO 02/20431 | 3/2002 |
| WO | WO 02/070682 A2 | 9/2002 |

OTHER PUBLICATIONS

K. Asami et al., "Real–Time Monitoring of Yeast Cell Division by Dielectric Spectroscopy", *Biophysical Journal*, 76, pp. 3345–3348 (1999).

(List continued on next page.)

*Primary Examiner*—Thurman K. Page
*Assistant Examiner*—Charesse Evans
(74) *Attorney, Agent, or Firm*—Fish & Neave; James F. Haley, Jr.; Z. Ying Li

(57) ABSTRACT

Compositions comprising a plurality of yeast cells, wherein said plurality of yeast cells are characterized by their ability to normalize the serum level of GPT, AP and/or LDH-5 in a mammal, said ability resulting from their having been cultured in the presence of an alternating electric field having a specific frequency and a specific field strength. Also included are methods of making and using these compositions.

9 Claims, 2 Drawing Sheets

OTHER PUBLICATIONS

E.K. Balcer–Kubiczek et al., "Expression Analysis of Human HL60 Cells Exposed to 60 Hz Square–or Sine–Wave Magnetic Fields", *Radiation Research*, 153, pp. 670–678 (2000).

C.A.L. Basset et al., "Beneficial Effects of Electromagnetic Fields", *Journal of Cellular Biochemistry*, 51, pp. 387–393 (1993).

P. Conti et al., "Effect of Electromagnetic Fields on Several CD Markers and Transcription and Expression of CD4", *Immunobiology*, 201, pp. 36–48 (1999).

A.M. Gonzalez et al., "Effects of an Electric Field of Sinusoidal Waves on the Amino Acid Biosynthesis by Azotobacter", *Z. Naturforsch*, 35, pp. 258–261 (1980).

E.M. Goodman et al., "Effects of Electromagnetic Fields on Molecules and Cells", *International Review of Cytology*, 158, pp. 279–339 (1995).

T. Grospietsch et al., "Stimulating Effects of Modulated 150 MHz Electromagnetic Fields on the Growth of *Escherichia coli* in a Cavity Resonator", *Bioelectrochemistry and Bioenergetics*, 37, pp. 17–23 (1995).

W. Grundler et al., "Nonthermal Effects of Millimeter Microwaves on Yeast Growth", *Z. Naturforsch*, 33, pp. 15–22 (1978).

W. Grundler et al., "Mechanisms of Electromagnetic Interaction with Cellular Systems", *Naturwissenschaften*, 79, pp. 551–559 (1992).

O.I. Ivaschuk et al., "Exposure of Nerve Growth Factor–Treated PC12 Rat Pheochromocytoma Cells to a Modulated Radiofrequency Field at 836.55 MHz: Effects on c–jun and c–fos Expression", *Bioelectromagnetics*, 18, pp. 223–229 (1997).

F. Jelínek et al., "Microelectronic Sensors for Measurement of Electromagnetic Fields of Living Cells and Experimental Results", *Bioelectrochemistry and Bioenergetics*, 48, pp. 261–266 (1999).

A. Lacy–Hulbert et al., "Biological Responses to Electromagnetic Fields", *FASEB Journal*, 12, pp. 395–420 (1998).

C.R. Libertin et al., "Effects of Gamma Rays, Ultraviolet Radiation, Sunlight, Microwaves and Electromagnetic Fields on Gene Expression Mediated by Human Immunodeficiency Virus Promoter", Radiation Research, 140, pp. 91–96 (1994).

H. Lin et al., "Specific Region of the c–myc Promoter Is Responsive to Electric and Magnetic Fields", *Journal of Cellular Biochemistry*, 54, pp. 281–288 (1994).

H. Lin et al., "Magnetic Field Activation of Protein–DNA Binding", *Journal of Cellular Biochemistry*, 70, pp. 297–303 (1998).

L.I. Loberg et al., "Expression of Cancer–Related Genes in Human Cells Exposed to 60 Hz Magnetic Fields", *Radiation Research*, 153, pp. 679–684 (2000).

R.L. Moore, "Biological Effects of Magnetic Fields: Studies with Microorganisms", *Canadian Journal of Microbiology*, 25, pp. 1145–1151 (1979).

C.A. Morehouse et al., "Exposure of Daudi Cells to Low–Frequency Magnetic Fields Does Not Elevate MYC Steady–State mRNA Levels", *Radiation Research*, 153, pp. 663–669 (2000).

V. Norris et al., "Do Bacteria Sing? Sonic Intercellular Communication Between Bacteria May Reflect Electromagnetic Intracellular Communication Involving Coherent Collective Vibrational Modes that Could Integrate Enzyme Activities and Gene Expression", *Molecular Microbiology*, 24, pp. 879–880 (1997).

G. Novelli et al., "Study of the Effects on DNA of Electromagnetic Fields Using Clamped Homogeneous Electric Field Gel Electrophoresis", *Biomedicine & Pharmacotherapy*, 45, pp. 451–454 (1991).

J.L. Phillips, "Effects of Electromagnetic Field Exposure on Gene Transcription", *Journal of Cellular Biochemistry*, 51, pp. 381–386 (1993).

V. Romano–Spica et al., "Ets1 Oncogene Induction by ELF–Modulated 50 MHz Radiofrequency Electromagnetic Field", *Bioelectromagnetics*, 21, pp. 8–18 (2000).

J.E. Trosko, "Human Health Consequences of Environmentally–Modulated Gene Expression: Potential Roles of ELF–EMF Induced Epigenetic Versus Mutagenic Mechanisms of Disease", *Bioelectromagnetics*, 21, pp. 402–406 (2000).

C. Ventura et al., "Elf–pulsed Magnetic Fields Modulate Opioid Peptide Gene Expression in Myocardial Cells", *Cardiovascular Research*, 45, pp. 1054–1064, (2000).

A.M. Woodward et al., "Genetic Programming as an Analytical Tool for Non–linear Dielectric Spectroscopy", *Bioelectrochemistry and Bioenergetics*, 48, pp. 389–396 (1999).

T. Yonetani et al., "Electromagnetic Properties of Hemoproteins", *The Journal of Biological Chemistry*, 247, pp. 2447–2455 (1972).

L. Zhang et al., "Electrostimulation of the Dehydrogenase System of Yeast by Alternating Currents", *Bioelectrochemistry and Bioenergetics*, 28, pp. 341–353 (1992).

Binninger, D. M. et al., "Effects of 60Hz AC magnetic fields on gene expression following exposure over multiple cell generations using *Saccharomyces cerevisiae*", *Biolectrochemistry and Bioenergetics*, 43(1): 83–89 (1997).

Deguchi, T. et al., "Nylon biodegradation by lignin–degrading fungi", *Applied and Environmental Microbiology*, 63(1): 329–331 (1997).

Pichko, V. B. et al., "Electromagnetic stimulation of productivity of microorganisms and its mechanisms", *Prikladnaya Biokhimiya I Mikrobiologiya*, 32(4): 468–472 (1996).

Ponne, C. T. et al., "Interaction of electromagnetic energy with biological material–relation to food processing", *Radiation Physics and Chemistry*, 45(4): 591–607 (1995).

Van Rensburg, P. et al., "Engineering yeast for efficient cellulose degradation", *Yeast*, 14(1): 67–76 (1998).

"*Saccharomyces cerevisiae* Meyen ex Hansen", China Catalogue of Cultures/China Committee of Culture Collection for Microorganisms (CCCCM), "www.im.ac.cn/database/YEAST/y122.htm", Apr. 24, 1996, retrieved on Nov. 27, 2002.

Van der Bogaerde J. et al., "Immune sensitization to food, yeast and bacteria in Crohn's disease," *Alimentary Pharmacology & Therapeutics*, 15:1647–1653 (2001).

Surawicz Christina M. et al., "The search for a better treatment for recurrent Clostridium difficile disease: Use of high–dose vancomycin combined with Saccharomyces boulardii," *Clinical Infectious Diseases*, 31:1012–1017 (2000).

Agarwal N. et al., "Selection of Saccharomyces cerevisiae strains for use as a microbial feed additive," *Letters in Applied Microbiology*, 31:270–273 (2000).

Grundler W. et al., "Resonant–like dependence at yeast growth rate on microwave frequencies," *The British Journal of Cancer*, Supplement, England Mar. 1982, 45–206–208 (1982).

Greenwalt C.J. et al., "Kombucha, the fermented tea: Microbiology, composition, and claimed health effects," *Journal of Food Protection*, 63:976–981 (2000).

Mayser P. et al., "The yeast spectrum of the [tea fungus Kokbucha]," *Mycoses*, Blackwell, Berlin, Germany, 38:289–295 (1995).

Durfresne C. et al., "Tea, Kombucha, and Health: A review," *Food Research International*, 33:409–421 (2000).

Liu C.H. et al., "The Isolation and identification of microbes from a fermented tea beverage, Haipao, and their interactions during Haipao fermentation," *Food Microbiology* (London), 13:407–145 (1996).

DIETARY SUPPLEMENTS BENEFICIAL FOR THE LIVER

FIELD OF THE INVENTION

The invention relates to compositions that are beneficial for the liver and useful as dietary supplements. These compositions contain yeast cells obtainable by growth in electromagnetic fields with specific frequencies and field strengths.

BACKGROUND OF THE INVENTION

There are various types of liver diseases, including acute hepatitis, chronic hepatitis, toxic liver injury, hepatic cancer, cirrhotic liver, fatty liver, portal hypertension, and the like. Liver disease in some patients develops into hepatic cirrhosis or even hepatic cancer after a period of time (A report by the research group on liver diseases, Health and Welfare Ministry, 1979). Prevention, observation, and cure of hepatitis are therefore important for preventing cirrhotic liver and hepatic cancer. In recent years, animal models of hepatitis and hepatic cancers have been developed and their application to the research of liver diseases is ongoing (Mori et al., Hepatic, Cholecyst, Pancresto 19(5):905–910 (1989)).

Rest and diet are principal means for curing acute hepatitis, while various other measures are taken to cure active-type chronic hepatitis, especially hepatitis B. Interferon, adenine arabinoside, and acyclovir have been used to treat hepatitis. However, prolonged use of these drugs causes severe side effects. Development of a treatment that is safe and effective for treating liver diseases is therefore strongly desired.

SUMMARY OF THE INVENTION

This invention is based on the discovery that certain yeast cells can be activated by electromagnetic fields having specific frequencies and field strengths to produce substances that are beneficial for the liver. Compositions comprising these activated yeast cells can be used as dietary supplements for improving liver health, e.g., alleviating symptoms of hepatitis, cirrhosis, fatty liver and other liver ailments.

This invention embraces a composition comprising a plurality of yeast cells that have been cultured in an alternating electric field having a frequency in the range of about 18000–18500 MHZ (e.g., 18180–18240 MHz), and a field intensity in the range of about 50 to 500 mV/cm (e.g., 100–450 mV/cm). The yeast cells are cultured in the alternating electric field for a period of time sufficient to substantially increase the capability of said plurality of yeast cells to produce substances beneficial for the liver. For instance, the cultured yeast cells when ingested can normalize the level of serum glutamate-pyruvate Transaminase (GPT), alkaline phosphatase (AP), and/or lactate dehydrogenase 5 (LDH-5) in a mammal.

The term "normalize" means changing the level of abnormally high or low concentrations of subject proteins in a mammal to a substantially normal level.

In one embodiment, the frequency and/or the field strength of the alternating electric field can be altered within the aforementioned ranges during said period of time. In other words, the yeast cells can be exposed to a series of electromagnetic fields. An exemplary period of time is about 40–100 hours (e.g., 50 to 80 hours).

Yeast cells that can be included in this composition can all be obtained from the China General Microbiological Culture Collection Center ("CGMCC"), a depository recognized under the Budapest Treaty (China Committee for Culture Collection of Microorganisms, Institute of Microbiology, Chinese Academy of Sciences, Haidian, P.O. BOX 2714, Beijing, 100080, China). Useful yeast species include, but are not limited to, *Saccharomyces cerevisiae, Saccharomyces carlsbergensis, Saccharomyces chevalieri, Saccharomyces delbrueckii, Saccharomyces exiguous, Saccharomyces fermentati, Saccharomyces logos, Saccharomyces mellis, Saccharomyces oviformis, Saccharomyces rosei, Saccharomyces rouxii, Saccharomyces sake, Saccharomyces uvarum, Saccharomyces willianus, Saccharomyces sp., Schizosaccharomyces octosporus, Schizosaccharomyces pombe, Sporobolomyces roseus, Torulopsis candida, Torulopsis famta, Torulopsis globosa, Torulopsis inconspicua, Trichosporon behrendii, Trichosporon capitatum, Trichosporon cutaneum, Wickerhamia fluoresens, Candida arborea, Candida krusei, Candida lambica, Candida lipolytica, Candida parapsilosis, Candida pulcherrima, Candida rugousa, Candida tropicalis, Candida utilis, Crebrothecium ashbyii, Geotrichum candidum, Hansenula anomala, Hansenula arabitolgens, Hansenula jadinii, Hansenula saturnus, Hansenula schneggii, Hansenula subpelliculosa, Kloeckera apiculata, Lipomyces starkeyi, Pichia farinosa, Pichia membranaefaciens, Rhodosporidium toruloides, Rhodotorula glutinis, Rhodotorula minuta, Rhodotorula rubar, Rhodotorula aurantiaca, Saccharomycodes ludwigii, and Saccharomycodes sinenses.* For instance, the yeast cells can be of the strain *Saccharomyces cerevisiae* Hansen AS2.375, AS2.501, AS2.502, AS2.503, AS2.504, AS2.535, AS2.558, AS2.560, AS2.561, AS2.562, or IFFI1048; or *Saccharomyces carlsbergensis* Hansen AS2.420, or AS2.444.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting. Throughout this specification and claims, the word "comprise," or variations such as "comprises" or "comprising" will be understood to imply the inclusion of a stated integer or group of integers but not the exclusion of any other integer or group of integers.

Other features and advantages of the invention will be apparent from the following detailed description, and from the claims.

DETAILED DESCRIPTION OF THE INVENTION

Figure 1:
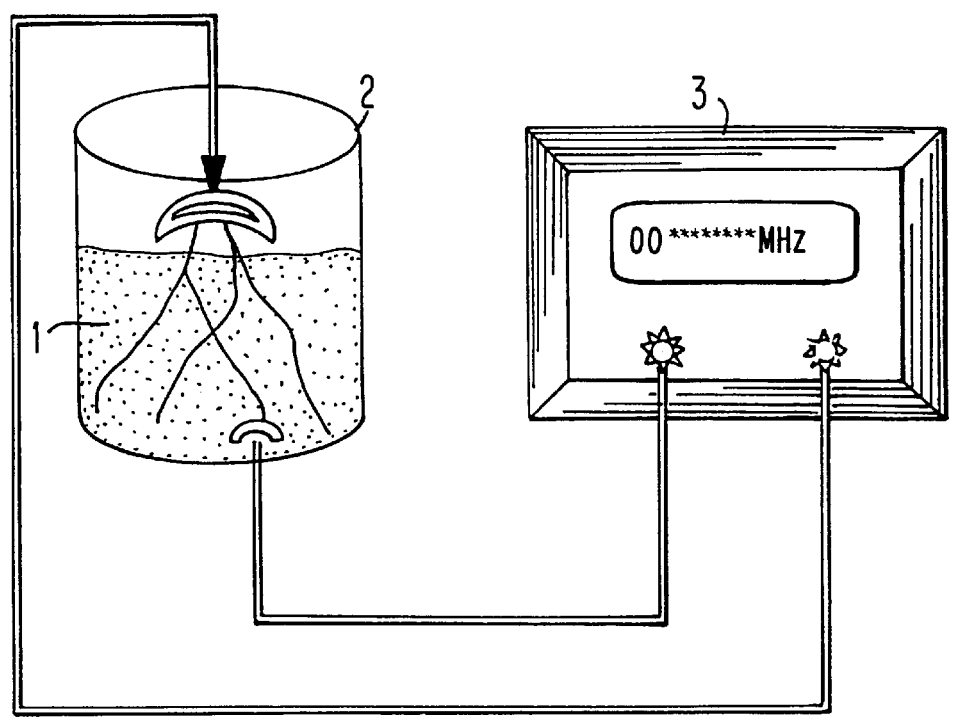
FIG. 1 is a schematic diagram showing an exemplary apparatus for activating yeast cells using electromagnetic fields. 1: yeast culture; 2: container; 3: power supply.

This invention is based on the discovery that certain yeast strains can be activated by electromagnetic fields ("EMF") having specific frequencies and field strengths to produce agents useful in treating liver ailments. Yeast compositions containing the activated yeast cells can be used as dietary supplements in the form of health drinks or pills. In certain embodiments, the yeast compositions of this invention can improve liver functions, thereby normalizing the serum levels of glutamate-pyruvate transaminase, alkaline phosphatase and/or lactate dehydrogenase 5.

Since the activated yeast cells contained in these yeast compositions have been cultured to endure acidic conditions (pH2.5–4.2), the compositions are stable in the stomach and can pass on to the intestines. Once in the intestines, the yeast cells are ruptured by various digestive enzymes, and the bioactive agents are released and readily absorbed.

Without being bound by any theory or mechanism, the inventor believes that EMFs activate or enhance the expression of a gene or a set of genes or alter the conformation and/or activity of certain cellular components (e.g. DNA, RNA, enzymes/proteins) in the yeast cells, resulting in the production of agents that are beneficial for the liver.

I. Yeast Strains Useful in the Invention

The types of yeasts useful in this invention include, but are not limited to, yeasts of the genera Saccharomyces, Candida, Crebrothecium, Geotrichum, Hansenula, Kloeckera, Lipomyces, Pichia, Rhodosporidium, Rhodotorula, Saccharomycodes, Schizosaccharomyces, Sporobolomyces, Torulopsis, Trichosporon, and Wickerhamia.

Exemplary species within the above-listed genera include, but are not limited to, the species illustrated in Table 1. Yeast strains useful in this invention can be obtained from laboratory cultures, or from publically accessible culture depositories, such as CGMCC and the American Type Culture Collection, 10801 University Boulevard, Manassas, Va. 20110-2209. Non-limiting examples of useful strains (with the accession numbers of CGMCC) are *Saccharomyces cerevisiae* Hansen AS2.375, AS2.501, AS2.502, AS2.503, AS2.504, AS2.535, AS2.558, AS2.560, AS2.561, AS2.562, and IFFI1048; and *Saccharomyces carlsbergensis* Hansen AS2.420 and AS2.444. Other non-limiting examples of useful strains are listed in Table 1. In general, yeast strains preferred in this invention are those used for fermentation in the food and wine industries. As a result, compositions containing these yeast cells are safe for human consumption.

Although it is preferred, the preparation of the yeast compositions of this invention is not limited to starting with a pure strain of yeast. A yeast composition of the invention may be produced by culturing a mixture of yeast cells of different species or strains.

TABLE 1

| Exemplary Yeast Strains | | | | |
|---|---|---|---|---|
| *Saccharomyces cerevisiae* Hansen | | | | |
| ACCC2034 | ACCC2035 | ACCC2036 | ACCC2037 | ACCC2038 |
| ACCC2039 | ACCC2040 | ACCC2041 | ACCC2042 | AS2. 1 |
| AS2. 4 | AS2. 11 | AS2. 14 | AS2. 16 | AS2. 56 |
| AS2. 69 | AS2. 70 | AS2. 93 | AS2. 98 | AS2. 101 |
| AS2. 109 | AS2. 110 | AS2. 112 | AS2. 139 | AS2. 173 |
| AS2. 174 | AS2. 182 | AS2. 196 | AS2. 242 | AS2. 336 |
| AS2. 346 | AS2. 369 | AS2. 374 | AS2. 375 | AS2. 379 |
| AS2. 380 | AS2. 382 | AS2. 390 | AS2. 393 | AS2. 395 |
| AS2. 396 | AS2. 397 | AS2. 398 | AS2. 399 | AS2. 400 |
| AS2. 406 | AS2. 408 | AS2. 409 | AS2. 413 | AS2. 414 |
| AS2. 415 | AS2. 416 | AS2. 422 | AS2. 423 | AS2. 430 |
| AS2. 431 | AS2. 432 | AS2. 451 | AS2. 452 | AS2. 453 |
| AS2. 458 | AS2. 460 | AS2. 463 | AS2. 467 | AS2. 486 |
| AS2. 501 | AS2. 502 | AS2. 503 | AS2. 504 | AS2. 516 |
| AS2. 535 | AS2. 536 | AS2. 558 | AS2. 560 | AS2. 561 |
| AS2. 562 | AS2. 576 | AS2. 593 | AS2. 594 | AS2. 614 |
| AS2. 620 | AS2. 628 | AS2. 631 | AS2. 666 | AS2. 982 |
| AS2. 1190 | AS2. 1364 | AS2. 1396 | IFFI1001 | IFFI1002 |
| IFFI1005 | IFFI1006 | IFFI1008 | IFFI1009 | IFFI1010 |
| IFFI1012 | IFFI1021 | IFFI1027 | IFFI1037 | IFFI1042 |
| IFFI1043 | IFFI1045 | IFFI1048 | IFFI1049 | IFFI1050 |
| IFFI1052 | IFFI1059 | IFFI1060 | IFFI1062 | IFFI1063 |
| IFFI1202 | IFFI1203 | IFFI1206 | IFFI1209 | IFFI1210 |
| IFFI12II | IFFI1212 | IFFI1213 | IFFI1214 | IFFI1215 |
| IFFI1220 | IFFI1221 | IFFI1224 | IFFI1247 | IFFI1248 |
| IFFI1251 | IFFI1270 | IFFI1277 | IFFI1287 | IFFI1289 |
| IFFI1290 | IFFI1291 | IFFI1292 | IFFI1293 | IFFI1297 |
| IFFI1300 | IFFI1301 | IFFI1302 | IFFI1307 | IFFI1308 |
| IFFI1309 | IFFI1310 | IFFI1311 | IFFI1331 | IFFI1335 |
| IFFI1336 | 1FFI1337 | IFFI1338 | IFFI1339 | IFFI1340 |
| IFFI1345 | IFFI1348 | IFFI1396 | IFFI1397 | 1FFI1399 |
| IFFI1411 | IFFI1413 | IFFI1441 | IFFI1443 | |
| *Saccharomyces cerevisiae* Hansen Var. *ellipsoideus* (Hansen) Dekker | | | | |
| ACCC2043 | AS2.2 | AS2.3 | AS2.8 | AS2.53 |
| AS2.163 | AS2.168 | AS2.483 | AS2.541 | AS2.559 |
| AS2.606 | AS2.607 | AS2.611 | AS2.612 | |
| *Saccharomyces chevalieri* Guilliermond | | | | |
| AS2.131 | AS2.213 | | | |
| *Saccharomyces delbrueckii* | | | | |
| AS2.285 | | | | |
| *Saccharomyces delbrueckii* Lindner ver. *mongolicus* (Saito) Lodder et van Rij | | | | |
| AS2.209 | AS2.1157 | | | |
| *Saccharomyces exiguous* Hansen | | | | |
| AS2.349 | AS2.1158 | | | |
| *Saccharomyces fermentati* (Saito) Lodder et van Rij | | | | |
| AS2.286 | AS2.343 | | | |
| *Saccharomyces logos* van laer et Denamur ex Jorgensen | | | | |
| AS2.156 | AS2.327 | AS2.335 | | |
| *Saccharomyces mellis* (Fabian et Quinet) Lodder et kreger van Rij | | | | |
| AS2.195 | | | | |
| *Saccharomyces mellis* Microellipsoides Osterwalder | | | | |
| AS2.699 | | | | |
| *Saccharomyces oviformis* Osteralder | | | | |
| AS2.100 | | | | |
| *Saccharomyces rosei* (Guilliermond) Lodder et Kreger van Rij | | | | |
| AS2.287 | | | | |
| *Saccharomyces rouxii* Boutroux | | | | |
| AS2.178 | AS2.180 | AS2.370 | AS2.371 | |
| *Saccharomyces sake* Yabe | | | | |
| ACCC2045 | | | | |
| *Candida arborea* | | | | |
| AS2.566 | | | | |
| *Candida lambica* (Lindner et Genoud) van. Uden et Buckley | | | | |
| AS2.1182 | | | | |
| *Candida krusei* (Castellani) Berkhout | | | | |

TABLE 1-continued

Exemplary Yeast Strains

AS2.1045
    *Candida lipolytica* (Harrison) Diddens et Lodder

AS2.1207    AS2.1216    AS2.1220    AS2.1379    AS2.1398
AS2.1399    AS2.1400
    *Candida parapsilosis* (Ashford) Langeron et Talice Var. *intermedia* Van Rij et Verona AS2.491
    *Candida parapsilosis* (Ashford) Langeron et Talice AS2.590
    *Candida pulcherrima* (Lindner) Windisch AS2.492
    *Candida rugousa* (Anderson) Diddens et Lodder AS2.511    AS2.1367    AS2.1369    AS2.1372    AS2.1373
AS2.1377    AS2.1378    AS2.1384
    *Candida tropicalis* (Castellani) Berkhout ACCC2004    ACCC2005    ACCC2006    AS2.164    AS2.402
AS2.564    AS2.565    AS2.567    AS2.568    AS2.617
AS2.637    AS2.1387    AS2.1397
    *Candida utilis* Henneberg Lodder et Kreger Van Rij AS2.120    AS2.281    AS2.1180
    *Crebrothecium ashbyii* (Guillermond)
    Routein (*Eremothecium ashbyii* Guilliermond)

AS2.481    AS2.482    AS2.1197
    Geotrichum candidum Link

ACCC2016    AS2.361    AS2.498    AS2.616    AS2.1035
AS2.1062    AS2.1080    AS2.1132    AS2.1175    AS2.1183
    *Hansenula anomala* (Hansen)H et P sydow ACCC2018    AS2.294    AS2.295    AS2.296    AS2.297
AS2.298    AS2.299    AS2.300    AS2.302    AS2.338
AS2.339    AS2.340    AS2.341    AS2.470    AS2.592
AS2.641    AS2.642    AS2.782    AS2.635    AS2.794
    *Hansenula arabitolgens* Fang AS2.887
    *Hansenula jadinii* (A. et R Sartory Weill et Meyer) Wickerham ACCC2019
    *Hansenula saturnus* (Klocker) H et P sydow ACCC2020
    *Hansenula schneggii* (Weber) Dekker AS2.304
    *Hansenula subpelliculosa* Bedford AS2.740    AS2.760    AS2.761    AS2.770    AS2.783
AS2.790    AS2.798    AS2.866
    *Kloeckera apiculata* (Reess emend. Klocker) Janke ACCC2022    ACCC2023    AS2.197    AS2.496    AS2.714
ACCC2021    AS2.711
    *Lipomycess starkeyi* Lodder et van Rij AS2.1390    ACCC2024
    *Pichia farinosa* (Lindner) Hansen ACCC2025    ACCC2026    AS2.86    AS2.87    AS2.705
AS2.803
    *Pichia membranaefaciens* Hansen ACCC2027    AS2.89    AS2.661    AS2.1039
    *Rhodosporidium toruloides* Banno ACCC2028
    *Rhodotorula glutinis* (Fresenius) Harrison

AS2.2029    AS2.280    ACCC2030    AS2.102    AS2.107

AS2.278    AS2.499    AS2.694    AS2.703    AS2.704
AS2.1146
    *Rhodotorula minuta* (Saito) Harrison AS2.277
    *Rhodotorula rubar* (Demme) Lodder AS2.21    AS2.22    AS2.103    AS2.105    AS2.108
AS2.140    AS2.166    AS2.167    AS2.272    AS2.279
AS2.282    ACCC2031
    *Rhodotorula aurantiaca* (Saito) Lodder AS2.102    AS2.107    AS2.278    AS2.499    AS2.694
AS2.703    AS2.704    AS2.1146
    *Saccharomyces carlsbergensis* Hansen AS2.113    ACCC2032    ACCC2033    AS2.312    AS2.116
AS2.118    AS2.121    AS2.132    AS2.162    AS2.189
AS2.200    AS2.216    AS2.265    AS2.377    AS2.417
AS2.420    AS2.440    AS2.441    AS2.443    AS2.444
AS2.459    AS2.595    AS2.605    AS2.638    AS2.742
AS2.745    AS2.748    AS2.1042
    *Saccharomyces uvarum* Beijer IFF11023    IFFI1032    IFFI1036    1FFI1044    IFFI1072
IFFI1205    IFFI1207
    *Saccharomyces willianus* Saccardo AS2.5    AS2.7    AS2.119    AS2.152    AS2.293
AS2.381    AS2.392    AS2.434    AS2.614    AS2.1189
    Saccharomyces sp.

AS2.31 1
    *Saccharomycodes ludwigii* Hansen

ACCC2044    AS2.243    AS2.508
    *Saccharomycodes sinenses* Yue

AS2.1395
    *Schizosaccharomyces octosporus* Beijerinck

ACCC2046    AS2.1148
    *Schizosaccharomyces pombe* Lindner

ACCC2047    ACCC2048    AS2.214    AS2.248    AS2.249
AS2.255    AS2.257    AS2.259    AS2.260    AS2.274
AS2.994    AS2.1043    AS2.1149    AS2.1178    IFFI1056
    *Sporobolomyces roseus* Kluyver et van Niel ACCC2049    ACCC2050    AS2.19    AS2.962    AS2.1036
ACCC2051    AS2.261    AS2.262
    *Torulopsis candida* (Saito) Lodder AS2.270    ACCC2052
    *Torulopsis famta* (Harrison) Lodder et van Rij ACCC2053    AS2.685
    *Torulopsis globosa* (Olson et Hammer) Lodder et van Rij ACCC2054    AS2.202
    *Torulopsis inconspicua* Lodder et Kreger van Rij AS2.75
    *Trichosporon behrendii* Lodder et. Kreger van Rij ACCC2056    AS2.1193
    *Trichosporon capitatum* Diddens et Lodder ACCC2056    AS2.1385
    *Trichosporon cutaneum* (de Beurm et al.) Ota ACCC2057    AS2.25    AS2.570    AS2.571    AS2.1374
    *Wickerhamia fluorescens* (Soneda) Soneda

ACCC2058    AS2.1388

II. Application of Electromagnetic Fields

An electromagnetic field useful in this invention can be generated and applied by various means well known in the art. For instance, the EMF can be generated by applying an alternating electric field or an oscillating magnetic field.

Alternating electric fields can be applied to cell cultures through electrodes in direct contact with the culture medium, or through electromagnetic induction. See, e.g., FIG. 1. Relatively high electric fields in the medium can be generated using a method in which the electrodes are in contact with the medium. Care must be taken to prevent electrolysis at the electrodes from introducing undesired ions into the culture and to prevent contact resistance, bubbles, or other features of electrolysis from dropping the field level below that intended. Electrodes should be matched to their environment, for example, using Ag-AgCl electrodes in solutions rich in chloride ions, and run at as low a voltage as possible. For general review, see Goodman et al., *Effects of EMF on Molecules and Cells*, International Review of Cytology, A Survey of Cell Biology, Vol. 158, Academic Press, 1995.

The EMFs useful in this invention can also be generated by applying an oscillating magnetic field. An oscillating magnetic field can be generated by oscillating electric currents going through Helmholtz coils. Such a magnetic field in turn induces an electric field.

The frequencies of EMFs useful in this invention range from about 18000 MHZ to 18500 MHZ. Exemplary frequencies include 18205, 18211, 18217, 18223, and 18227 MHZ. The field strength of the electric field useful in this invention ranges from about 100 to 450 mV/cm (e.g., 100–150, 210–260, 300–340, or 380–420 mV/cm). Exemplary field strengths include 240, 248, 408, 415, and 315 mV/cm.

When a series of EMFs are applied to a yeast culture, the yeast culture can remain in the same container while the same set of EMF generator and emitters is used to change the frequency and/or field strength. The EMFs in the series can each have a different frequency or a different field strength; or a different frequency and a different field strength. Such frequencies and field strengths are preferably within the above-described ranges. Although any practical number of EMFs can be used in a series, it may be preferred that the yeast culture be exposed to a total of 2, 3, 4, 5, 6, 7, 8, 9 or 10 EMFs in a series.

Although the yeast cells can be activated after even a few hours of culturing in the presence of an EMF, it may be preferred that the activated yeast cells be allowed to multiply and grow in the presence of the EMF(s) for a total of 40–100 hours.

FIG. 1 illustrates an exemplary apparatus for generating alternating electric fields. An electric field of a desired frequency and intensity can be generated by an AC source (3) capable of generating an alternating electric field, preferably in a sinusoidal wave form, in the frequency range of 5 to 20,000 MHZ. Signal generators capable of generating signals with a narrower frequency range can also be used. If desired, a signal amplifier can also be used to increase the output. The culture container (2) can be made from a non-conductive material, e.g., glass, plastic or ceramic. The cable connecting the culture container (2) and the signal generator (3) is preferably a high frequency coaxial cable with a transmission frequency of at least 30 GHz.

The alternating electric field can be applied to the culture by a variety of means, including placing the yeast culture (1) in close proximity to the signal emitters such as a metal wire or tube capable of transmitting EMFs. The metal wire or tube can be made of red copper, and be placed inside the container (2), reaching as deep as 3–30 cm. For example, if the fluid in the container (2) has a depth of 15–20 cm, 20–30 cm, 30–50 cm, 50–70 cm, 70–100 cm, 100–150 cm or 150–200 cm, the metal wire can be 3–5 cm, 5–7 cm, 7–10 cm, 10–15 cm, 15–20 cm, 20–30 cm and 25–30 cm from the bottom of the container (2), respectively. The number of metal wires/tubes used can be from 1 to 10 (e.g., 2 to 3). It is recommended, though not mandated, that for a culture having a volume up to 10 L, metal wires/tubes having a diameter of 0.5 to 2 mm be used. For a culture having a volume of 10–100 L, metal wires/tubes having a diameter of 3 to 5 mm can be used. For a culture having a volume of 100–1000 L, metal wires/tubes having a diameter of 6 to 15 mm can be used. For a culture having a volume greater than 1000 L, metal wires/tubes having a diameter of 20–25 mm can be used.

In one embodiment, the electric field is applied by electrodes submerged in the culture (1). In this embodiment, one of the electrodes can be a metal plate placed on the bottom of the container (2), and the other electrode can comprise a plurality of electrode wires evenly distributed in the culture (1) so as to achieve even distribution of the electric field energy. The number of electrode wires used depends on the volume of the culture as well as the diameter of the wires.

III. Culture Media

Culture media useful in this invention contain sources of nutrients that can be assimilated by yeast cells. Complex carbon-containing substances in a suitable form (e.g., carbohydrates such as sucrose, glucose, dextrose, maltose and xylose) can be the carbon sources for yeast cells. The exact quantity of the carbon sources can be adjusted in accordance with the other ingredients of the medium. In general, the amount of carbohydrate varies between about 0.1% and 10% by weight of the medium and preferably between about 0.1% and 5%, and most preferably about 2%. These carbon sources can be used individually or in combination. Amino acid-containing substances such as beef extract and peptone can also be added. In general, the amount of amino acid containing substances varies between about 0.1% and 1% by weight of the medium and preferably between about 0.1% and 0.5%. Among the inorganic salts which can be added to a culture medium are the customary salts capable of yielding sodium, potassium, calcium, phosphate, sulfate, carbonate, and like ions. Non-limiting examples of nutrient inorganic salts are $(NH_4)_2HPO_4$, $CaCO_3$, $KH_2PO_4$, $K_2HPO_4$, $MgSO_4$, NaCl, and $CaSO_4$.

IV. Electromagnetic Activation of Yeast Cells

To activate or enhance the ability of yeast cells to produce agents beneficial for the gastrointestinal system, these cells can be cultured in an appropriate medium under sterile conditions at 20–35° C. (e.g., 28–32° C.) for a sufficient amount of time (e.g., 10–150 hours) in an alternating electric field or a series of alternating electric fields as described above.

An exemplary set-up of the culture process is depicted in FIG. 1 (see above). An exemplary culture medium contains the following per 1000 ml of sterile water: 20 g of sucrose, 40 μg of Vitamin B1, 50 μg of Vitamin B6, 0.2 g of $KH_2PO_4$, 0.2 g of $MgSO_4.7H_2O$, 0.25 g of NaCl, 0.1 g of $CaSO_4.2H_2O$, 3 g of $CaCO_3.5H_2O$, and 2.5 g of peptone. Yeast cells of the desired strain(s) are then added to the culture medium to form a mixture containing $1\times10^8$ cells per 1000 ml of culture medium. The yeast cells can be of any of the strains listed in Table 1. The mixture is then added to the apparatus shown in FIG. 1.

The activation process of the yeast cells involves the following steps: (1) maintaining the temperature of the activation apparatus at 24–33° C. (e.g., 28–32° C.), and culturing the yeast cells for 30–42 hours (e.g., 38 hours); (2) applying an alternating electric field having a frequency of 18205 MHZ and a field strength of 210–260 mV/cm (e.g., 239–241 mV/cm) for 13–20 hours (e.g., 15 hours); (3) then applying an alternating electric field having a frequency of 18211 MHZ and a field strength of 220–260 mV/cm (e.g., 247–249 mV/cm) for 15–25 hours (e.g., 19 hours); (4) then applying an alternating electric field having a frequency of 18217 MHZ and a field strength of 380–420 mV/cm (e.g., 406–410 mV/cm) for 20–30 hours (e.g., 25 hours); (5) then applying an alternating electric field having a frequency of 18223 MHZ and a field strength of 380–420 mV/cm (e.g., 413–417 mV/cm) for 9–12 hours (e.g., 10 hours); and (6) then applying an alternating electric field having a frequency of 18227 MHZ and a field strength of 300–330 mV/cm (e.g., 313–317 mV/cm) for 9–12 hours (e.g., 10 hours). The activated yeast cells are then recovered from the culture medium by various methods known in the art, dried (e.g., by lyophilization) and stored at 4° C. Preferably, the concentration of the dried yeast cells are no less than $10^{10}$ cells/g.

V. Acclimatization of Yeast Cells to the Gastric Environment

Because the yeast compositions of this invention must pass through the stomach before reaching the small intestine, where the effective components are released from these yeast cells, it is preferred that these yeast cells be cultured under acidic conditions to acclimatize the cells to the gastric juice. This acclimatization process results in better viability of the yeast cells in the acidic gastric environment.

To achieve this, the yeast powder containing activated yeast cells can be mixed with a highly acidic acclimatizing culture medium at 10 g (containing more than $10^{10}$ activated cells per gram) per 1000 ml. The yeast mixture is then cultured first in the presence of an alternating electric field having a frequency of 18223 MHZ and a field strength of 390–420 mV/cm (e.g., 403–407 mV/cm) at about 28 to 32° C. for 25 to 48 hours (e.g., 46 hours). The resultant yeast cells can then be further incubated in the presence of an alternating electric field having a frequency of 18227 MHZ and a field strength of 300–330 mV/cm (e.g., 315–319 mV/cm) at about 28 to 32° C. for 15 to 25 hours (e.g., 20 hours). The resulting acclimatized yeast cells are then either dried and stored in powder form ($\geq 10^{10}$ cells/g) at room temperature or in vacuum at 0–4° C.

An exemplary acclimatizing culture medium is made by mixing 700 ml fresh pig gastric juice and 300 ml wild Chinese hawthorn extract. The pH of the acclimatizing culture medium is adjusted to 2.5 with 0.1 M hydrochloric acid (HCl) and/or 0.2 M potassium biphthalate ($C_6H_4$(COOK)COOH). The fresh pig gastric juice is prepared as follows. At about 4 months of age, newborn Holland white pigs are sacrificed, and the entire contents of their stomachs are retrieved and mixed with 2000 ml of water under sterile conditions. The mixture is then allowed to stand for 6 hours at 4° C. under sterile conditions to precipitate food debris. The supernatant is collected for use in the acclimatizing culture medium. To prepare the wild Chinese hawthorn extract, 500 g of fresh wild Chinese hawthorn is dried under sterile conditions to reduce water content ($\leq 8\%$). The dried fruit is then ground ($\geq 20$ mesh) and added to 1500 ml of sterile water. The hawthorn slurry is allowed to stand for 6 hours at 4° C. under sterile conditions. The hawthorn supernatant is collected to be used in the acclimatizing culture medium.

VI. Manufacture of Yeast Compositions

Figure 2:
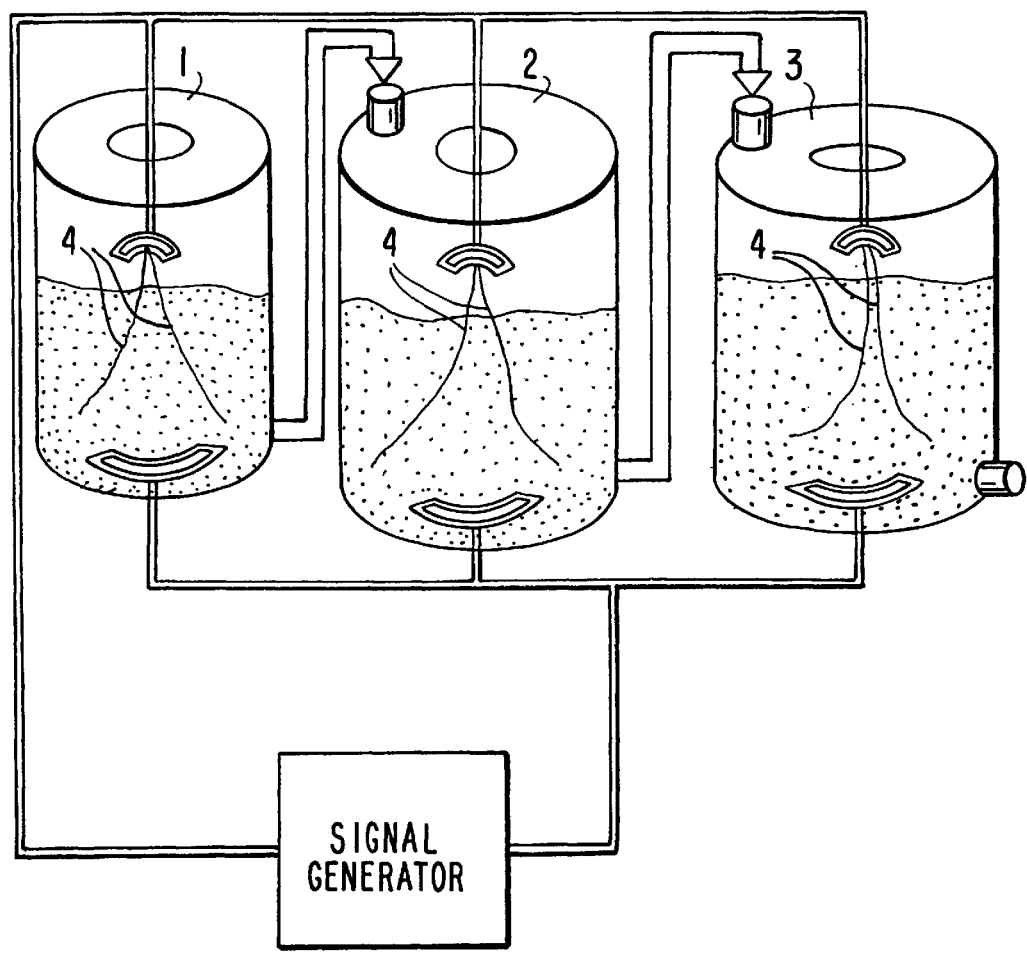
FIG. 2 is a schematic diagram showing an exemplary apparatus for making yeast compositions of the invention. The apparatus comprises a signal generator and interconnected containers 1, 2 and 3.

To manufacture the yeast compositions of the invention, an apparatus depicted in FIG. 2 or an equivalent thereof can be used. This apparatus includes three containers, a first container (1), a second container (2), and a third container (3), each equipped with a pair of electrodes (4). One of the electrodes is a metal plate placed on the bottom of the containers, and the other electrode comprises a plurality of electrode wires evenly distributed in the space within the container to achieve even distribution of the electric field energy. All three pairs of electrodes are connected to a common signal generator.

The culture medium used for this purpose is a mixed fruit extract solution containing the following ingredients per 1000 L: 300 L of wild Chinese hawthorn extract, 300 L of jujube extract, 300 L of Wu Wei Zi (*Schisandra chinensis* (Turez) Baill seeds) extract, and 100 L of soy bean extract. To prepare hawthorn, jujube and Wu Wei Zi extracts, the fresh fruits are washed and dried under sterile conditions to reduce the water content to no higher than 8%. One hundred kilograms of the dried fruits are then ground ($\geq 20$ mesh) and added to 400 L of sterile water. The mixtures are stirred under sterile conditions at room temperature for twelve hours, and then centrifuged at 1000 rpm to remove insoluble residues. To make the soy bean extract, fresh soy beans are washed and dried under sterile conditions to reduce the water content to no higher than 8%. Thirty kilograms of dried soy beans are then ground into particles of no smaller than 20 mesh, and added to 130 L of sterile water. The mixture is stirred under sterile conditions at room temperature for twelve hours and then centrifuged at 1000 rpm to remove insoluble residues. To make the culture medium, these extracts are mixed according to the above recipe, and the mixture is autoclaved at 121° C. for 30 minutes and cooled to below 40° C. before use.

One thousand grams of the activated yeast powder prepared as described above (Section V, supra) is added to 1000 L of the mixed fruit extract solution, and the yeast solution is transferred to the first container (1) shown in FIG. 2. The yeast cells are then cultured in the presence of an alternating electric field having a frequency of 18223 MHZ and a field strength of about 390–420 mV/cm (e.g., 403–407 mV/cm) at 28–32° C. under sterile conditions for 16 hours. The yeast cells are further incubated in an alternating electric field having a frequency of 18227 MHZ and a field strength of 320–350 mV/cm (e.g., 333–337 mV/cm). The culturing continues for another 12 hours.

The yeast culture is then transferred from the first container (1) to the second container (2) which contains 1000 L of culture medium (if need be, a new batch of yeast culture can be started in the now available first container (1)), and subjected to an alternating electric field having a frequency of 18223 MHZ and a field strength of 200–220 mV/cm (e.g., 206–210 mV/cm) for 10 hours. Subsequently the frequency and field strength of the electric field are changed to 18227 MHZ and 210–230 mV/cm (e.g., 213–217 mV/cm), respectively. The culturing continues for another ten hours.

The yeast culture is then transferred from the second container (2) to the third container (3) which contains 1000

L of culture medium, and subjected to an alternating electric field having a frequency of 18223 MHZ and a field strength of 90–110 mV/cm (e.g., 104–108 mV/cm) for 12 hours. Subsequently the frequency and field strength of the electric field are changed to 18227 MHZ and 100–120 mV/cm (e.g., 103–107 mV/cm), respectively. The culturing continues for another 8 hours.

The yeast culture from the third container (3) can then be packaged into vacuum sealed bottles for use as dietary supplement, e.g., health drinks. If desired, the final yeast culture can also be dried within 24 hours and stored in powder form. The dietary supplement can be taken three to four times daily at 30–60 ml/dose for a three-month period, preferably 10–30 minutes before meals and at bedtime.

In some embodiments, the compositions of the invention can also be administered intravenously or peritoneally in the form of a sterile injectable preparation. Such a sterile preparation can be prepared as follows. A sterilized health drink composition is first treated under ultrasound (1000 Hz) for 10 minutes and then centrifuged at 4355 g for another 10 minutes. The resulting supernatant is adjusted to pH 7.2–7.4 using 1 M NaOH and subsequently filtered through a membrane (0.22 μm for intravenous injection and 0.45 μm for peritoneal injection) under sterile conditions. The resulting sterile preparation is submerged in a 35–38° C. water bath for 30 minutes before use.

The yeast compositions of the present invention are derived from yeasts used in food and pharmaceutical industries. The yeast compositions are thus devoid of side effects associated with many pharmaceutical compounds

VII. EXAMPLES

The following examples are meant to illustrate the methods and materials of the present invention. Suitable modifications and adaptations of the described conditions and parameters which are obvious to those skilled in the art are within the spirit and scope of the present invention.

The activated yeast compositions used in the following experiments were prepared as described above, using *Saccharomyces cerevisiae* Hansen AS2.560 cells cultured in the presence of an alternating electric field having the electric field frequency and field strength exemplified in the parentheses following the recommended ranges listed in Section IV, supra. Control yeast compositions were those prepared in the same manner except that the yeast cells were cultured in the absence of EMFs. Unless otherwise indicated, the yeast compositions and the corresponding controls were administered to the animals by intragastric feeding.

Example 1

Serum Glutamate-pyruvate Transaminase Activity

Glutamate-pyruvate transaminase (GPT) normally is expressed in hepatocytes. When the liver tissue undergoes necrosis or is otherwise damaged, GPT is released into the blood stream, elevating the level of serum GPT. Thus, the serum GPT level is one of the important indicators of liver functions.

In this study, 32 Wistar rats (170–200 g, 8–10 months old) were divided into 4 groups, each having 4 females and 4 males. Rats in group A were each given 3 ml of the activated yeast composition once daily for 8 days. On days 1 and 5, the rats were also injected with 5 mg of carbon tetrachloride per kilogram body weight. Rats in groups B and C were treated in the same manner except that the rats were given the control yeast composition and saline, respectively, in lieu of the activated yeast composition. Rats in group D were treated in the same manner as group C except that no carbon tetrachloride was administered. On day 8, the rats were sacrificed, and their blood was drawn to determine serum GPT levels.

To do so, 0.1 ml of serum from each animal was mixed with 0.5 ml of the glutamate-pyruvate substrate solution (1 M) and incubated in a 37° C. water bath for 30 minutes. Then 0.5 ml of 2,4-dinitrophenylhydrazine was added and the incubation continued for another 20 minutes. Finally 5 ml of 0.4 M NaOH was added. The control reaction was prepared in the same manner except that the serum was added immediately after, not before, the 30 minute incubation step. The optical density of the sample was measured at 520 nm, using the control reaction for calibration. The GPT concentration was determined by using a standard curve. The data are shown in Table 2 below.

TABLE 2

| Group | Number of animals | Serum GTP |
|---|---|---|
| A | 8 | 61.3 ± 18.64 |
| B | 8 | 279.6 ± 132.38 |
| C | 8 | 288.5 ± 126.83 |
| D | 8 | 101.6 ± 32.07 |

The data demonstrate that the activated yeast composition significantly restored serum GPT to normal levels in rats treated with carbon tetrachloride.

Example 2

Activity of Serum Alkaline Phosphatase

Serum alkaline phosphatase (AP) is produced mainly by the liver. The level of serum AP is an indicator of the liver health, with an elevated level suggesting an unhealthy liver.

In this study, 32 male Sprague-Dawley rats (120–150 g) were divided into 4 equal groups. Rats in group A were each given 3 ml of the activated yeast composition daily for 13 days. Every three days during this time period, the animals were also injected with 2 mg of liquid paraffin containing 15% carbon tetrachloride per kg body weight (four times total). Rats in groups B and C were treated in the same manner, except that they were given the control yeast composition and saline, respectively, in lieu of the activated yeast composition. Rats in group D were treated in the same manner as group C except that no paraffin injection was made.

On day 13, after the last $CCl_4$ injection, the animals were fasted for 16 hours. Then the animals were sacrificed, and their serum GPT and AP levels determined. GPT levels were determined as described above. To determine AP levels, 0.1 ml of serum from the animal was mixed with 4 ml of the AP substrate solution and incubated in a 37° C. water bath for 7 minutes. Then 1 ml of 0.6% 4-AAP (alanine aminopeptidase) and 1 ml of 4.8% $K_3Fe(CN)_6$ were added. The standard was prepared in the same manner except that PHEN standard solution was used in lieu of serum. For blank control, no serum or PHEN solution was added.

The optical density of the sample was then measured at 500 nm, using the blank control to calibrate the spectrophotometer. Alkaline phosphatase (AP) activity was calculated as [(OD of test sample)/(OD of standard)]×10. The experimental data are shown in Table 3 below.

TABLE 3

| Group | Number of Animals | Serum GPT (units/ml serum) | AP (units/ 100 ml serum) | Liver weight (g/100 g body weight) |
|---|---|---|---|---|
| A | 8 | 42.2 ± 19.4 | 33.6 ± 5.2 | 3.81 ± 0.21 |
| B | 8 | 162.9 ± 78.3 | 55.9 ± 7.2 | 5.07 ± 0.19 |
| C | 8 | 167.4 ± 89.5 | 57.4 ± 5.5 | 5.19 ± 0.25 |
| D | 8 | 27.3 ± 7.3 | 42.2 ± 12.0 | 3.72 ± 0.30 |

These results indicate that, unlike the control yeast composition, the activated yeast composition of this invention normalized serum GPT and AP levels in rats injected with liver-damaging agents.

Example 3

Activity of Lactate Dehydrogenase 5

An elevated level of lactate dehydrogenase 5 (LDH-5) often accompanies hepatitis caused by hepatitis B virus. In this experiment, the effectiveness of the activated yeast composition in treating hepatitis in a mouse model was assessed.

Liver extract prepared from hybrid mice was used to immunize pure-bred mice to induce chronic hepatitis. Specifically, livers from hybrid mice were minced and centrifuged in a refrigerated centrifuge at 10,000 g for 30 minutes. The supernatant was collected and mixed with Freund's complete adjuvant to form an emulsion for injection into newly weaned male C57BL mice.

Forty newly weaned C57BL mice were divided into four equal groups. Mice in group A were each administered 1 ml of the activated yeast composition daily for 9 weeks. During the first five weeks, the mice were each injected with 0.1 ml of the liver extract emulsion twice weekly. During the remaining four weeks, the injection was administered once weekly. Mice in groups B and C were treated in the same manner, except that the control yeast composition and saline, respectively, were used in lieu of the activated yeast composition. Mice in group D were treated in the same manner as group C, except that no injection of liver emulsion was administered.

Twenty-four hours after the last day of treatment, the animals were sacrificed and their blood sera were collected. LDH-5 was isolated from the serum using cellulose acetate electrophoresis. And the CICs (circulating immune complexes) were measured by PEG (polyethylene glycol) precipitation method. The results are shown in Table 4 below.

TABLE 4

| Group | Number of Animals | LDH-5 (ug/L) | CLC OD |
|---|---|---|---|
| A | 10 | 61 ± 5.21 | 0.025 ± 0.003 |
| B | 10 | 94 ± 7.31 | 0.059 ± 0.007 |
| C | 10 | 93 ± 6.41 | 0.061 ± 0.007 |
| D | 10 | 58 ± 2.47 | 0.023 ± 0.002 |

These data demonstrate that the activated yeast composition arkedly reduced serum LDH-5 and CLC levels in mice with induced hepatitis, as compared to control.

While a number of embodiments of this invention have been set forth, it is apparent that the basic constructions may be altered to provide other embodiments which utilize the compositions and methods of this invention.

What is claimed is:

1. A composition comprising a plurality of yeast cells, wherein said plurality of yeast cells are characterized by their ability to normalize the level of serum glutamate-pyruvate Transaminase (GPT), alkaline phosphatase (AP), or lactate dehydrogenase 5 (LDH-5) in a mammal, said ability resulting from their having been cultured in the presence of an alternating electric field having a frequency in the range of 18180–18240 MHZ and a field strength in the range of 100–450 mV/cm, as compared to yeast cells not having been so cultured.

2. The composition of claim 1, wherein said frequency is in the range of 18205 to 18227 MHZ.

3. The composition of claim 1, wherein said field strength is in the range of 210 to 420 mV/cm.

4. The composition of claim 1, wherein said yeast cells are of the species selected from the group consisting of Saccharomyces cerevisiae, Saccharomyces carlsbergensis, Saccharomyces chevalieri, Saccharomyces delbrueckii, Saccharomyces exiguous, Saccharomyces fermentati, Saccharomyces logos, Saccharomyces mellis, Saccharomyces oviformis, Saccharomyces rosei, Saccharomyces rouxii, Saccharomyces sake, Saccharomyces uvarum, Saccharomyces willianus, Saccharomyces sp., Schizosaccharomyces octosporus, Schizosaccharomyces pombe, Sporobolomyces roseus, Torulopsis candida, Torulopsis famta, Torulopsis globosa, Torulopsis inconspicua, Trichosporon behrendii, Trichosporon capitatum, Trichosporon cutaneum, Wickerhamia fluoresens, Candida arborea, Candida krusei, Candida lambica, Candida lipolytica, Candida parapsilosis, Candida pulcherrima, Candida rugousa, Candida tropicalis, Candida utilis, Crebrothecium ashbyii, Geotrichum candidum, Hansenula anomala, Hansenula arabitolgens, Hansenula jadinii, Hansenula saturnus, Hansenula schneggii, Hansenula subpelliculosa, Kloeckera apiculata, Lipomyces starkeyi, Pichia farinosa, Pichia membranaefaciens, Rhodosporidium toruloides, Rhodotorula glutinis, Rhodotorula minuta, Rhodotorula rubar, Rhodotorula aurantiaca, Saccharomycodes ludwigii, and Saccharomycodes sinenses.

5. The composition of claim 1, wherein said yeast cells are of the strain deposited at the China General Microbiological Culture Collection Center with an accession number selected from the group consisting of Saccharomyces cerevisiae Hansen AS2.375, AS2.501, AS2.502, AS2.503, AS2.504, AS2.535, AS2.558, AS2.560, AS2.561, AS2.562 and IFFI1048, and Saccharomyces carlsbergensis Hansen AS2.420 and AS2.444.

6. The composition of claim 1, wherein said composition is in the form of a tablet, powder, or a health drink.

7. The composition of claim 1, wherein said composition is in the form of a health drink.

8. A method of treating hepatitis in a subject, comprising introducing orally the composition of claim 1 to the subject.

9. A method of preparing a yeast composition, comprising culturing a plurality of yeast cells in the presence of an alternating electric field having a frequency in the range of 18180–18240 MHZ and a field strength in the range of 100–450 mV/cm for a period of time sufficient to substantially increase the capability of said plurality of yeast cells to normalize the level of serum GPT, AP, or LDH-5 in a mammal with liver problems.

* * * * *